(12) United States Patent
Reed et al.

(10) Patent No.: US 12,296,109 B2
(45) Date of Patent: May 13, 2025

(54) INJECTION MOLDED CANNULA AND METHOD FOR MAKING SAME

(71) Applicant: Becton, Dickinson and Company, Franklin Lakes, NJ (US)

(72) Inventors: Jeff Reed, Minden, NE (US); Andrew Allegretti, New York, NY (US); Jean-Pierre Karam, Lake Forest, IL (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 713 days.

(21) Appl. No.: 17/299,860

(22) PCT Filed: Dec. 6, 2019

(86) PCT No.: PCT/US2019/064881
§ 371 (c)(1),
(2) Date: Jun. 4, 2021

(87) PCT Pub. No.: WO2020/118156
PCT Pub. Date: Jun. 11, 2020

(65) Prior Publication Data
US 2022/0040446 A1 Feb. 10, 2022

Related U.S. Application Data

(60) Provisional application No. 62/776,562, filed on Dec. 7, 2018.

(51) Int. Cl.
*A61M 25/00* (2006.01)
*B29C 45/26* (2006.01)
(Continued)

(52) U.S. Cl.
CPC ......... *A61M 25/0009* (2013.01); *B29C 45/26* (2013.01); *A61M 2005/1586* (2013.01); *A61M 2005/1587* (2013.01); *A61M 25/0012* (2013.01); *A61M 25/0015* (2013.01); *A61M 25/01* (2013.01); *A61M 2039/1072* (2013.01); *A61M 2207/10* (2013.01); *B29L 2031/7548* (2013.01)

(58) Field of Classification Search
CPC .............. A61M 25/0009; A61M 25/01; A61M 25/0015; A61M 25/0012; A61M 2005/1586; A61M 2005/1587; A61M 2039/1072; A61M 2207/10; B29C 45/26; B29L 2031/7548
USPC ..................................... 264/328.1
See application file for complete search history.

(56) References Cited

U.S. PATENT DOCUMENTS 9,463,314 B2    10/2016  Drake et al.
2005/0245895 A1* 11/2005  Haider .................. A61M 5/148
                                                604/93.01

(Continued)

FOREIGN PATENT DOCUMENTS

| CN | 101827620 A | 9/2010 | |
|---|---|---|---|
| EP | 1222937 A1 * | 7/2002 | ......... A61M 25/065 |
| WO | WO-2007021449 A2 | 2/2007 | |

*Primary Examiner* — Galen H Hauth
*Assistant Examiner* — Lawrence D. Hohenbrink, Jr.
(74) *Attorney, Agent, or Firm* — Dickinson Wright PLLC (57) ABSTRACT

A method, including the operations of molding a hollow cannula to create flash on the cannula at parting lines of a mold, retaining the flash on the cannula, and installing the cannula with the flash in a medical device.

14 Claims, 9 Drawing Sheets

(51) Int. Cl.
     *A61M 5/158*    (2006.01)
     *A61M 25/01*    (2006.01)
     *A61M 39/10*    (2006.01)
     *B29L 31/00*    (2006.01)

(56) References Cited

U.S. PATENT DOCUMENTS

| | | |
|---|---|---|
| 2009/0157007 A1* | 6/2009 | McKinnon ........ A61M 25/0014 |
| | | 604/177 |
| 2009/0203953 A1 | 8/2009 | Lamoureux et al. |
| 2013/0013054 A1* | 1/2013 | Clarke ...................... A61F 2/07 |
| | | 623/1.15 |
| 2016/0001063 A1 | 1/2016 | Drake et al. |
| 2016/0262785 A1 | 9/2016 | Dubois et al. |
| 2016/0296728 A1 | 10/2016 | Smith |
| 2017/0020729 A1 | 1/2017 | Jarrett et al. |
| 2018/0161522 A1* | 6/2018 | Sanders .............. A61M 5/3245 |

* cited by examiner

INJECTION MOLDED CANNULA AND METHOD FOR MAKING SAME

CROSS-REFERENCE TO RELATED APPLICATION

This application claims priority under 35 USC § 119(e) from U.S. provisional patent application Ser. No. 62/776,562, filed on Dec. 7, 2018, the disclosure of which is incorporated herein by reference in its entirety.

FIELD OF THE INVENTION

The present invention relates to medical devices, and more particularly, to medical devices with molded hollow cannulas, and to methods for making such medical devices and cannulas.

BACKGROUND OF THE INVENTION

One mode of insulin infusion treatment includes infusion pump therapy via a catheter, needle, or other type of cannula. Infusion pumps offer the advantages of continuous infusion of insulin, precision dosing, and programmable delivery schedules, Together, these advantages result in more accurate blood glucose control. In this mode of insulin infusion treatment, the infusion pump remains attached to the user and required doses of insulin are delivered to the user via the pump.

One type of cannula is a catheter, which generally is a tube that can be inserted into the body to permit the administration of fluids. In infusion pump therapy, the types and sizes of the catheter may vary, but generally, the catheter is a thin, flexible tube. In some uses, however, it may be larger and/or rigid. A rigid, hollow, metal needle may also be used in place of a soft plastic catheter.

One type of conventional infusion set is sold as the Quick-Set® infusion set by Medtronic. In such devices, the infusion pump includes a catheter assembly connected to a pump via a tubing set, and a separate insertion device inserts and/or attaches the catheter assembly into/to a user via an introducer needle provided as part of the infusion set. The infusion set and insertion device can also be combined, as in the Mio® infusion set sold by Medtronic, which is an "all-in-one" design that combines the infusion set and insertion device into one unit.

Another type of insulin infusion device, known as a "patch pump," has recently become available. Unlike a conventional infusion pump, a patch pump is an integrated device that combines most or all of the fluid components in a single housing that is adhesively attached to an infusion site, and does not require the use of a separate infusion (tubing) set, A patch pump adheres to the skin, contains insulin (or other medication), and delivers the drug over a period of time, either transdermally, or via an integrated subcutaneous mini-catheter. Some patch pumps communicate with a separate controller device wirelessly (such as one sold under the brand name OmniPod®), while others are completely self-contained.

A conventional infusion device can include a fluid connector, which may be releasably attached to a base that can be secured to a user's skin. An infusion pump supplies fluid to a catheter via the fluid connector/base engagement.

As previously noted, medical devices that are intended to deliver medicament or monitor patient conditions over an extended period of time, are designed to be worn by the patient, and have a cannula that is inserted through the patient's skin for delivering the medicament. One way to manufacture such devices is extrude a cannula via dies and pins, and secure the cannula in the device using a metal or plastic wedge. But such extrusion processes can be slow and unpredictable, and can be a bottleneck for production.

SUMMARY OF EMBODIMENTS OF THE INVENTION

Accordingly, it is an aspect of the present invention to provide a method of molding a cannula.

The foregoing and/or other aspects of the present invention are achieved by providing a method, including the operations of molding a hollow cannula to create flash on the cannula at parting lines of a mold, retaining the flash on the cannula, and installing the cannula with the flash in a medical device.

The foregoing and/or other aspects of the present invention are also achieved by providing a method, including the operations of designing a mold for molding a cannula for a medical device so that an intentional flash is formed at parting lines of the mold during molding of a cannula, molding a cannula using the mold; maintaining the flash on the molded cannula after the molding, and installing the molded cannula with the flash in a medical device.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

The embodiments are not intended to be mutually exclusive; features of one embodiment can be combined with other embodiments as long as they do not contradict each other.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as "up," "down," "bottom," "top," "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely.

Figure 1:
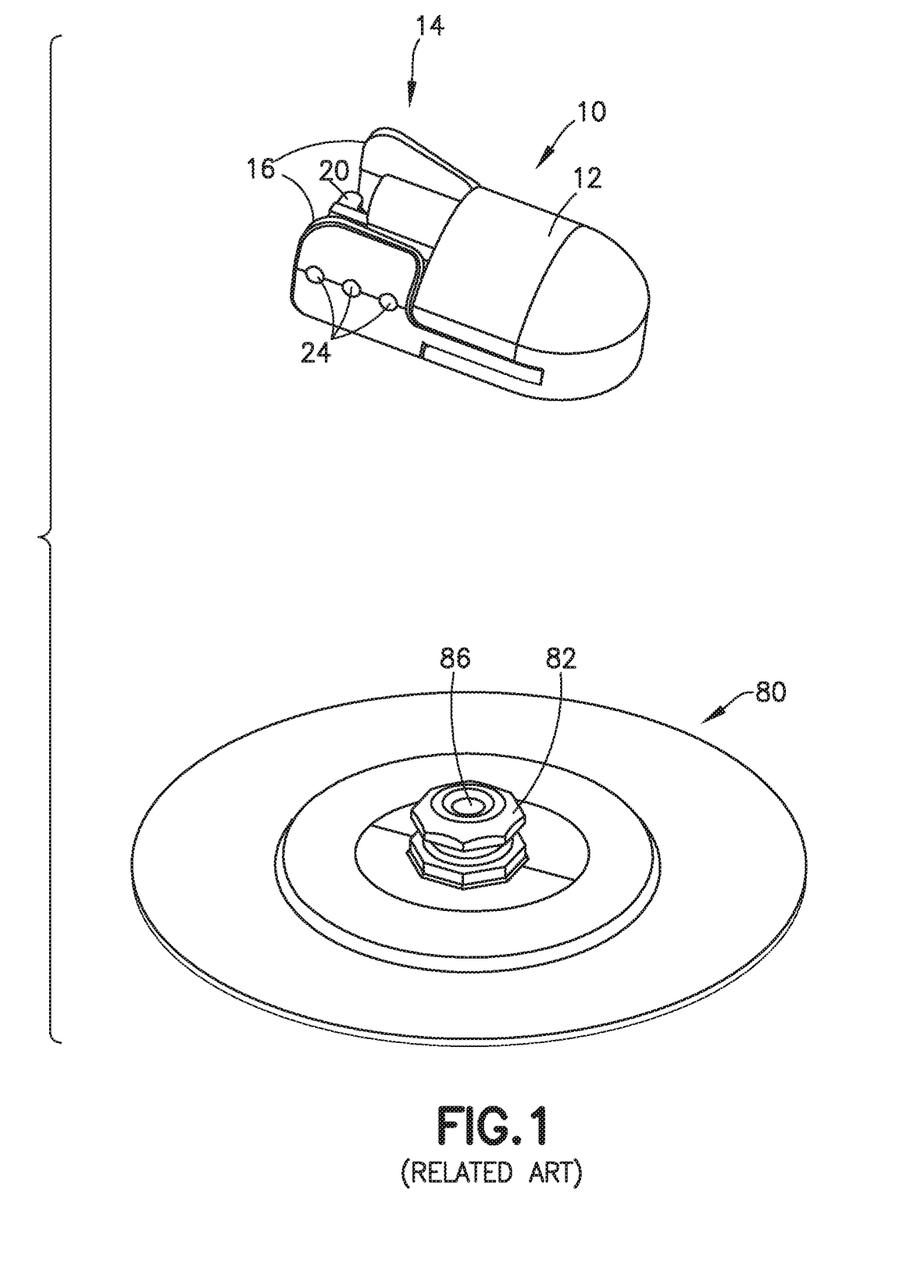
FIGS. 1-3 are various views of a related art fluid connector and an associated base.
Figure 2:
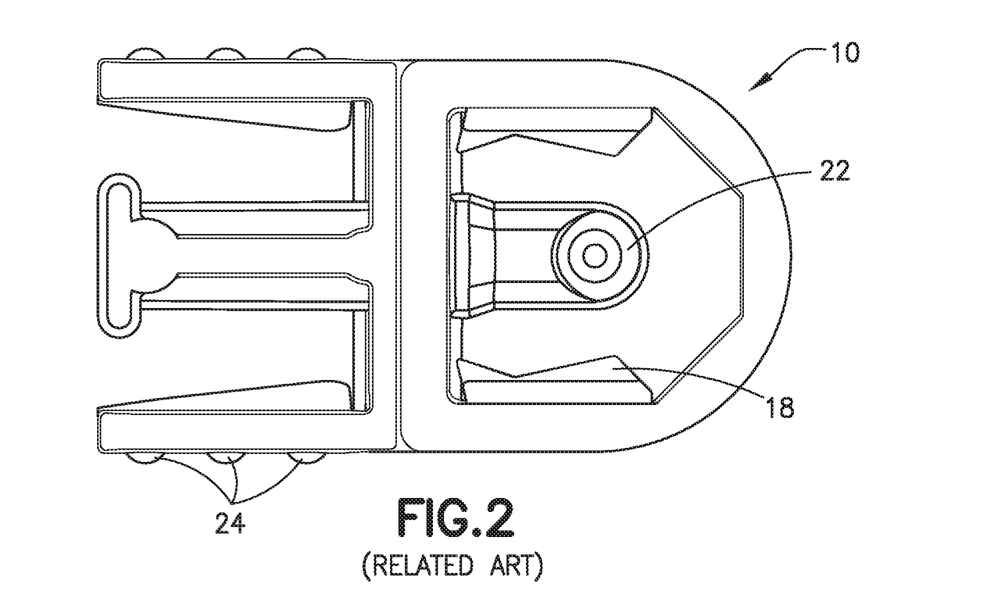
Figure 3:
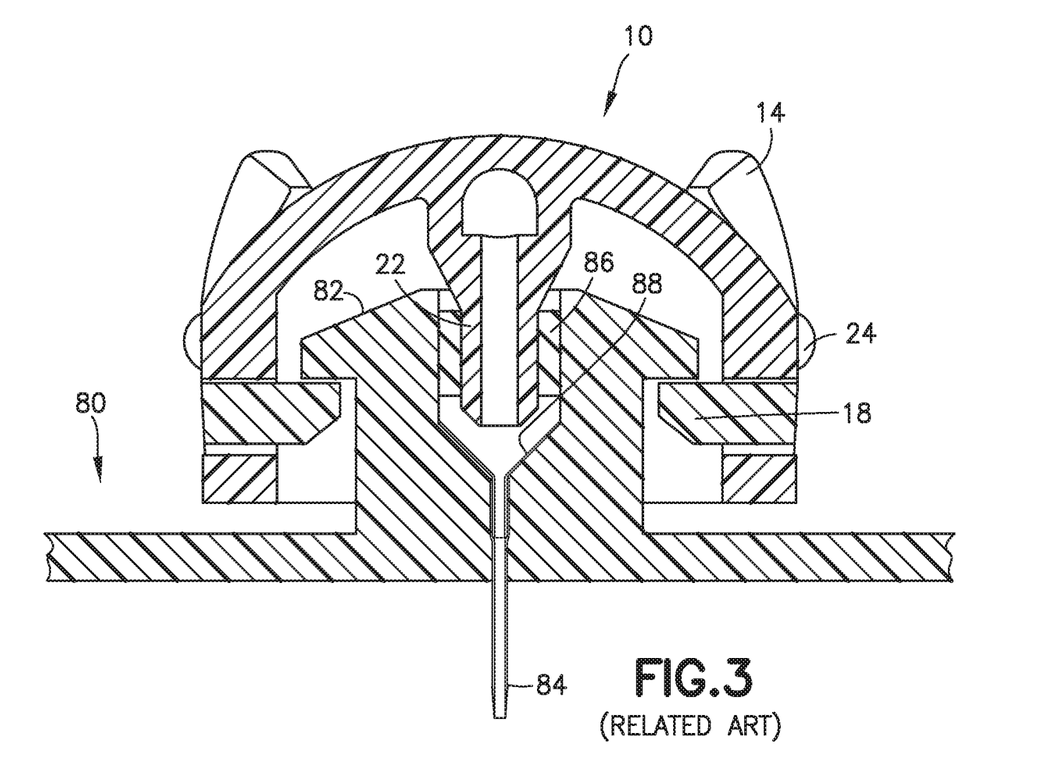

FIG. 1 is a perspective view of a related art two-piece fluid connector 10 and associated base 80, such as those found in PCT Publication WO 2013/086463, the disclosure of which is incorporated herein by reference for this purpose. FIG. 2 is a bottom view of the fluid connector 10, and FIG. 3 is a cross-sectional view of the fluid connector 10 connected with the base 80. The fluid connector 10 includes two components: a fluid path portion 12, and a latching portion 14. Together, the fluid path portion 12 and the latching portion 14 form a housing 15. The latching portion 14 includes activation levers 16, fluid connector latches 18, and a rigid stop 20.

The fluid path portion 12 includes a tubing connector portion 22 for connecting the fluid connector 10 with tubing. The fluid path portion 12 can be secured to the latching portion 14 via snap-fit engagement.

As shown in FIGS. 1, 2 and 3, the fluid path portion 12 has a blunt cannula 22 extending distally from a proximal interior surface of the housing 15. When connected to a corresponding base 80 with a patient cannula 84 that has been inserted into the user's skin, the blunt cannula 22 pierces a septum 86 in a mushroom-shaped head 82 of the base 80 to fluidly connect a pump with the patient cannula 84 on the distal side of the base 80. The patient cannula 84 is flexible, and is held in the base 80 by a metal wedge. Typically, the patient cannula 84 is inserted into a patient's skin using a known insertion device.

Figure 4:
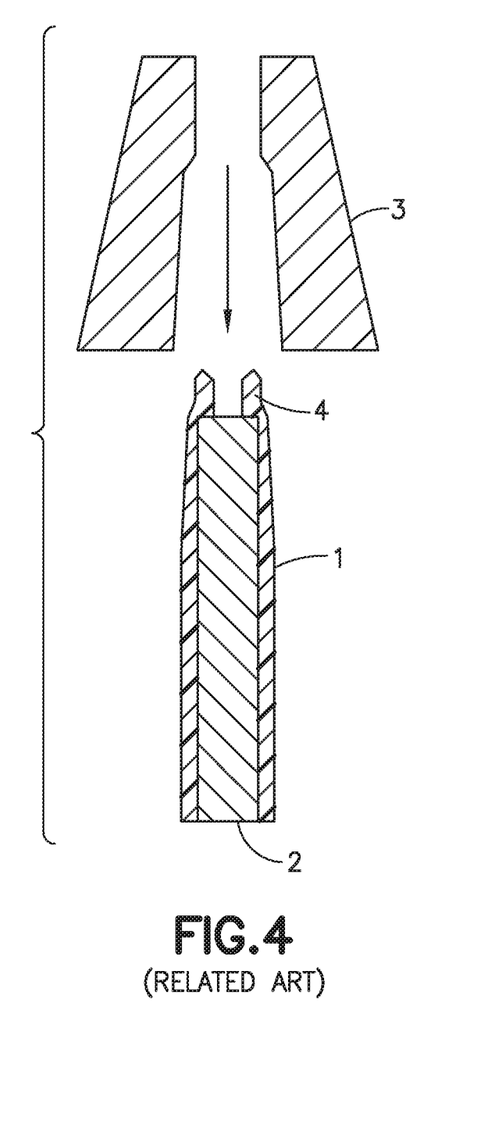
FIG. 4 is a cross-sectional view of a related art mold and cannula.

Injection molding is a known process that uses molds that wear down over time. Once worn, the injected material plastic) seeps out of the mold cavity at joint lines or parting lines, and forms what is known as "flash" at edges of the molded part. In current practices, such flash is undesirable, and is removed after removing the molded object from the mold, for example, as described in U.S. Pat. No. 5,736,085 issued on Apr. 7, 1998 to Brown et al. Brown discloses a catheter with flash, generally shown in FIG. 1, comprising a catheter 1 that is molded from a material, such as plastic. Flash 4 is produced on each side of the catheter 1 at the mold's parting line. The flash 4 is trimmed from the catheter 1 using a die to punch the flash 4 from the catheter 1. Flash can also be trimmed using a cutting tool or a laser.

In embodiments of the present invention, the molds are designed specifically to create a purposeful flash edge profile on the injection molded catheter. For example, this can be done by controlling the tolerances of the mold (e.g., the tightness of the interface between the two mold halves) to promote the formation of the flash edges. More specifically, for a typical mold, there is a gap of about 0.0004 inches (about 0.0102 mm) between mated mold halves. This small space permits air to escape the mold as the plastic or other material is, for example, injected into the mold, but is too small for the plastic to escape from the mold. A molder can, for example, widen this gap using, for example, an end mill or an electrode, along a subsection of the mold that forms a longitudinal portion of the cannula. If the gap along corresponding portions of each mold half is widened to about 0.0007 inches (about 0.0178 mm) along a subsection of the longitudinal portion of the cannula, the resulting gap in the mated mold would be about 0.0014 inches (0.0356 mm), ticks would be sufficient to allow some plastic to escape and form the flash.

Figure 5:
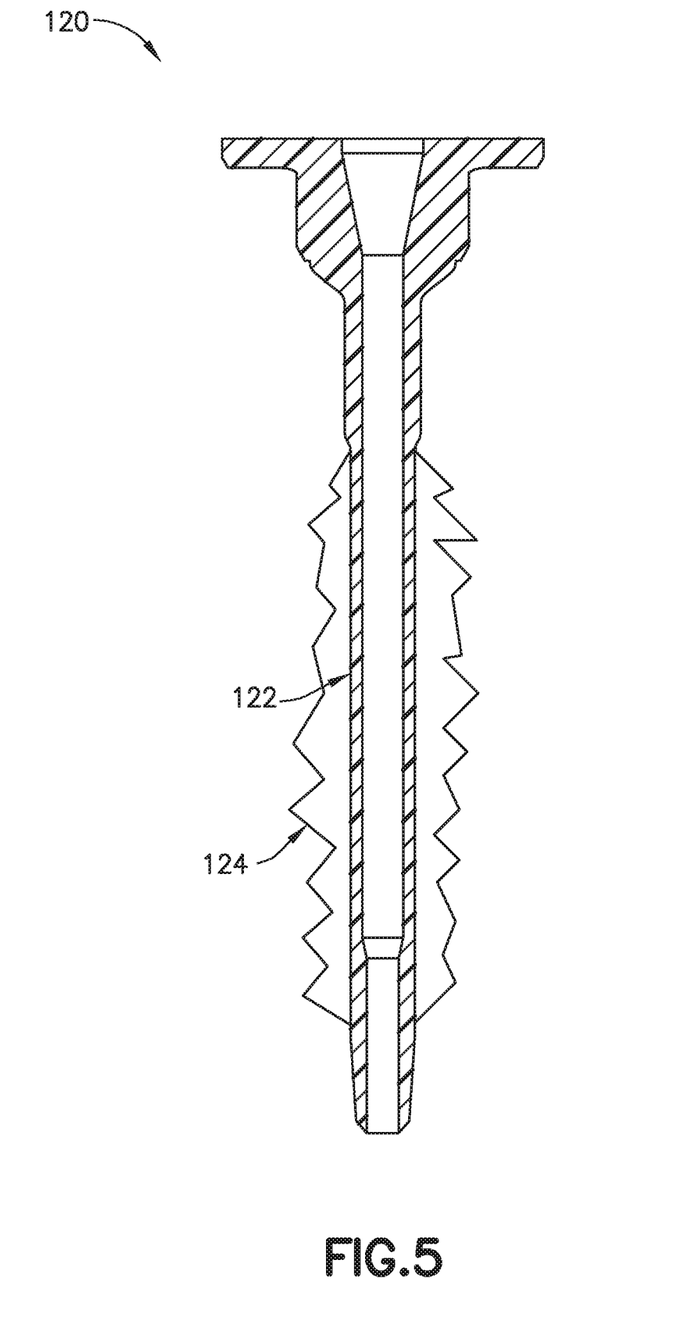
FIG. 5 is a cross-sectional view of a cannula assembly in accordance with an embodiment of the present invention.

As shown in FIG. 5, the cannula with flash assembly, generally shown at 120, comprises a hollow cannula 122 that is molded using a material, such as plastic. Flash 124 is produced on opposing sides of the cannula 122 at the parting line of the mold. In embodiments of the present invention, the flash 124 remains on the cannula 122 as the final product, and the flash 124 acts as a cutting edge for improved insertion of the cannula into a patient. The molding can be, for example, injection molding. According to one embodiment, the entire flash is maintained on the cannula. According to another embodiment, the flash 124 can be modified subsequent to removal from the mold.

As a result of the manufacturing process previously described, the flash 124 tapers down as it extends radially form the cannula 122, and thus, the flash 124 edge profile is designed to be bladelike, and may decrease the amount of force required to insert the cannula. According to one embodiment, as shown in FIG. 5, the flash edge is serrated.

According to another embodiment, the flash 124 edge is smooth, or not serrated. This can be accomplished by laterally mismatching the mold halves. In other words, the two mold halves meet along a plane. By laterally sliding one of the mold halves along the plane by a small amount (e.g., around $\frac{1}{32}$ to $\frac{1}{2}$ of a diameter of the cannula) or laterally offsetting one of the mold halves by the small about prior to mating the halves, a smooth flash following the shape of the molded item (cannula) can be produced. The smooth flash on one side of the cannula would be produced by one of the mold halves, and the smooth flash on the opposite side of the cannula would be produced by the other one of the mold halves.

Figure 6:
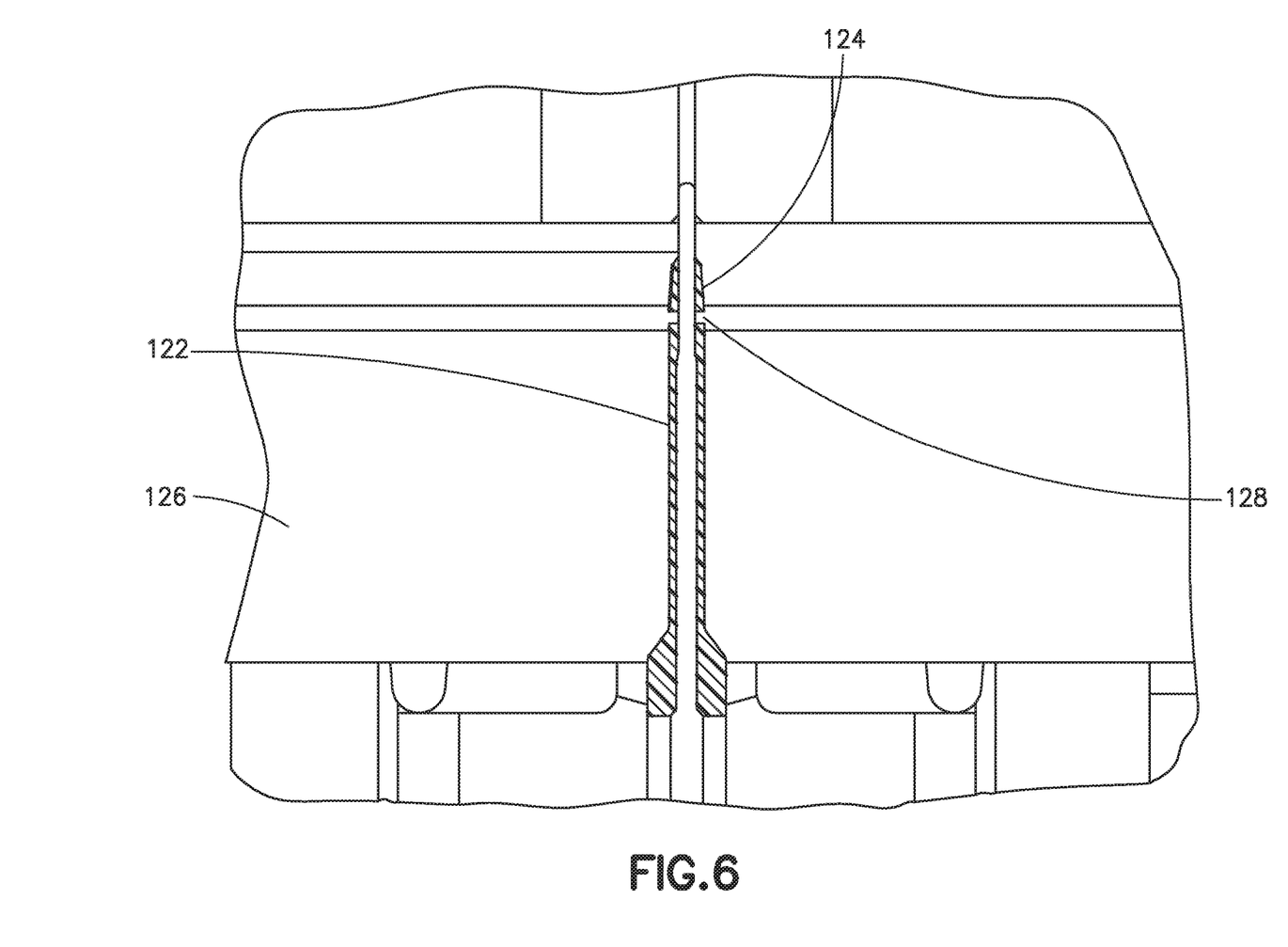
FIG. 6 is a cross-sectional view of a mold and a cannula in accordance with another embodiment of the present invention.

As shown in FIG. 6, the cannula 122 can be molded with one or more side ports 128.

In such embodiments, by material choice, the cannula 122 can be made sufficiently stiff that a metal wedge is not needed to hold the cannula 122 in a medical device, such as the base 180. In such an embodiment, rather than in a metal wedge, a septum 186, can be installed directly in the one-piece injection molded cannula 22 to seal a fluid path. Such an embodiment would reduce the number of parts needed for a device, and would speed production.

Figure 7:
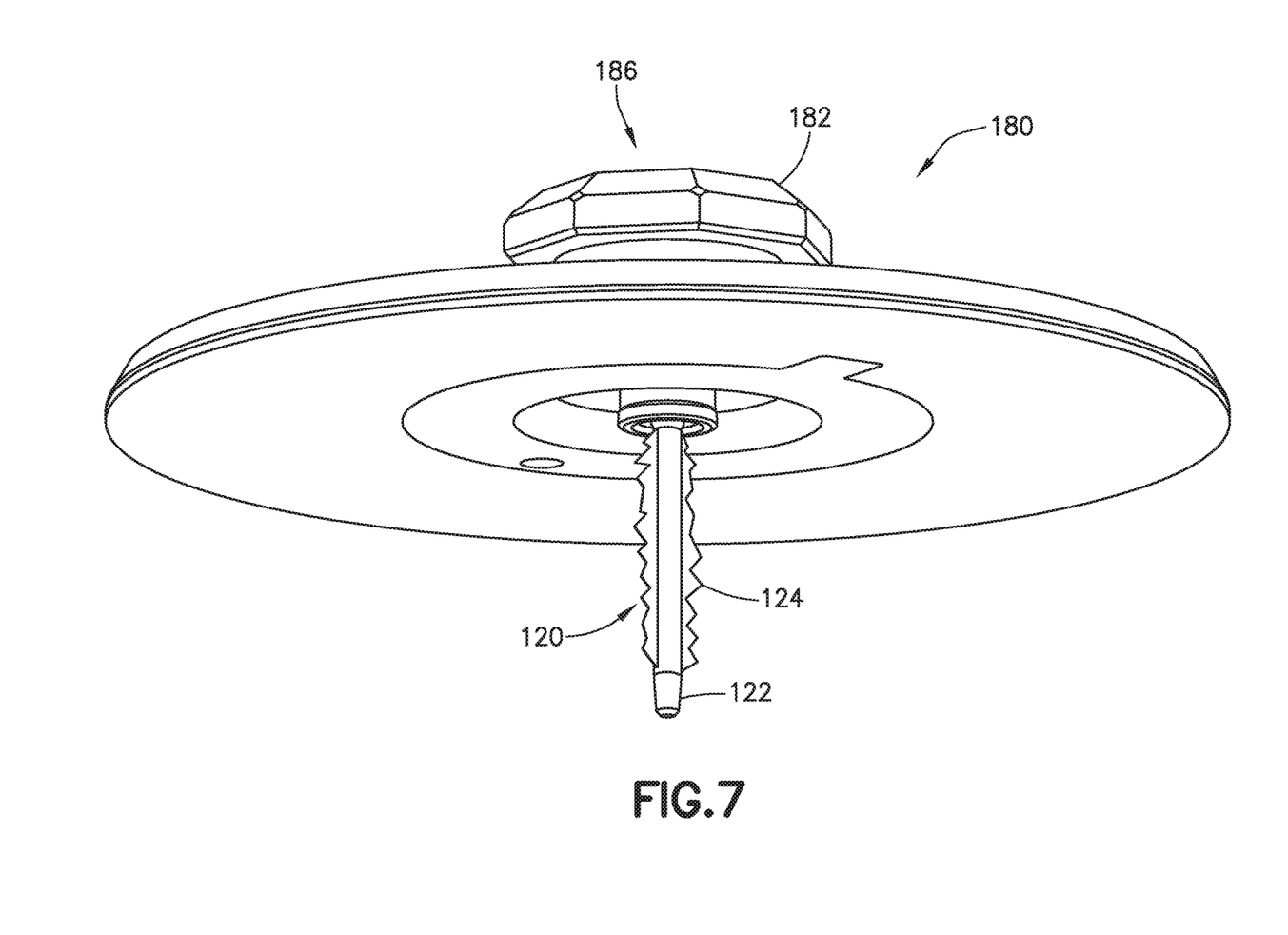
FIG. 7 is a perspective view of a medical device in accordance with embodiment of the present invention incorporating the cannula assembly of FIG. 5.
Figure 8:
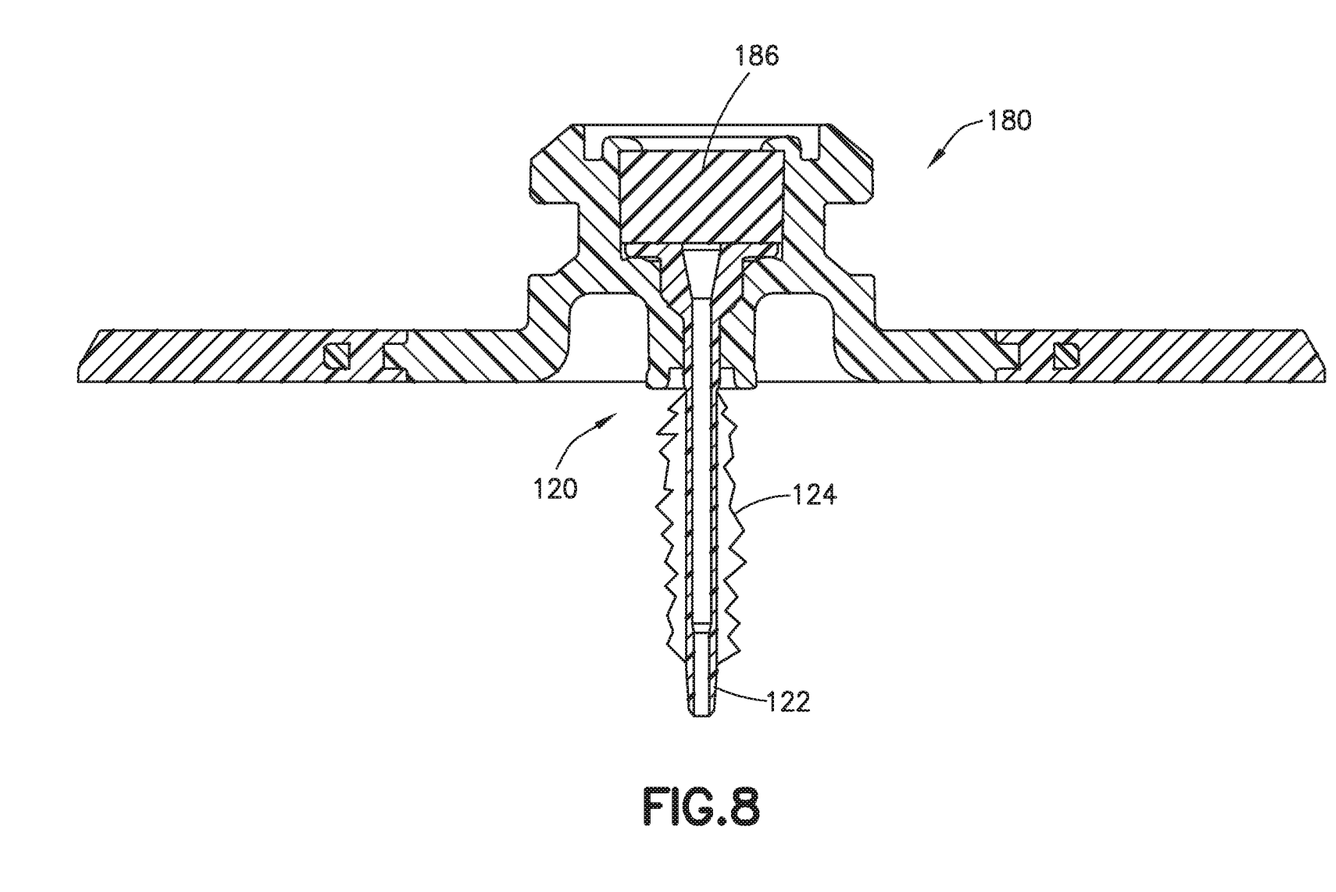
FIG. 8 is a cross-sectional view of the device of FIG. 7.

FIG. 7 is a perspective view of a medical device 180 in accordance with embodiment of the present invention, and FIG. 8 is a cross-sectional view of the device. More specifically, the medical device 180 is a base of infusion device similar to the previously described base 80. The base 180, however, incorporates the hollow cannula member 120. As shown in FIGS. 7 and 8, the cannula member 120 extends distally from the distal side of the base 180. In addition, for the one-piece cannula member 120, no metal wedge is needed to hold the cannula member 120 in the base 180. The size of the flash 124 in FIGS. 5, 7, and 8 is slightly exaggerated for clarity and illustration. According to one embodiment, an average radial dimension of the flash 124 is about 1/32 to 1/2 of the diameter of the portion of the cannula 122 that extends from the base 180.

The flash 124 on the cannula member 120 may sufficiently reduce the force required for insertion into a patient's skin that an insertion device might not be needed. Alternatively, the base 180 may be inserted using a known inserter and introducer needle, but the flash 124 may ease insertion and reduce patient pain.

Figure 9:
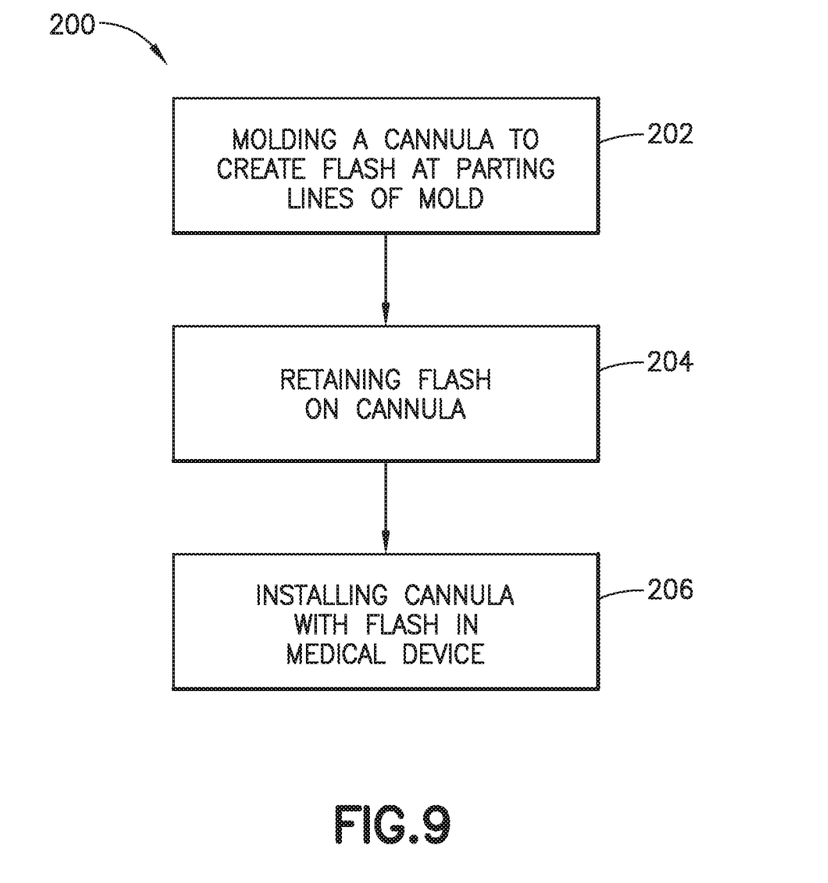
FIGS. 9 and 10 are flow charts of methods in accordance with embodiments of the present invention.

FIG. 9 is a flow chart illustrating a method 200 in accordance with an embodiment of the present invention. Operation 202 is molding a cannula to create flash at parting lines of a mold. Operation 204 is retaining the flash on the cannula, and operation 206 is installing the cannula with flash in a medical device, such as base 180. According to one embodiment, the cannula is installed in the medical device without modifying the flash. The method 200 can include other operations, such as packaging the medical device having the cannula with the flash. According to one embodiment, the medical device is packaged without having modified the flash. The method can also include removing the medical device from the packaging, and inserting the cannula with the flash into a patient.

Figure 10:
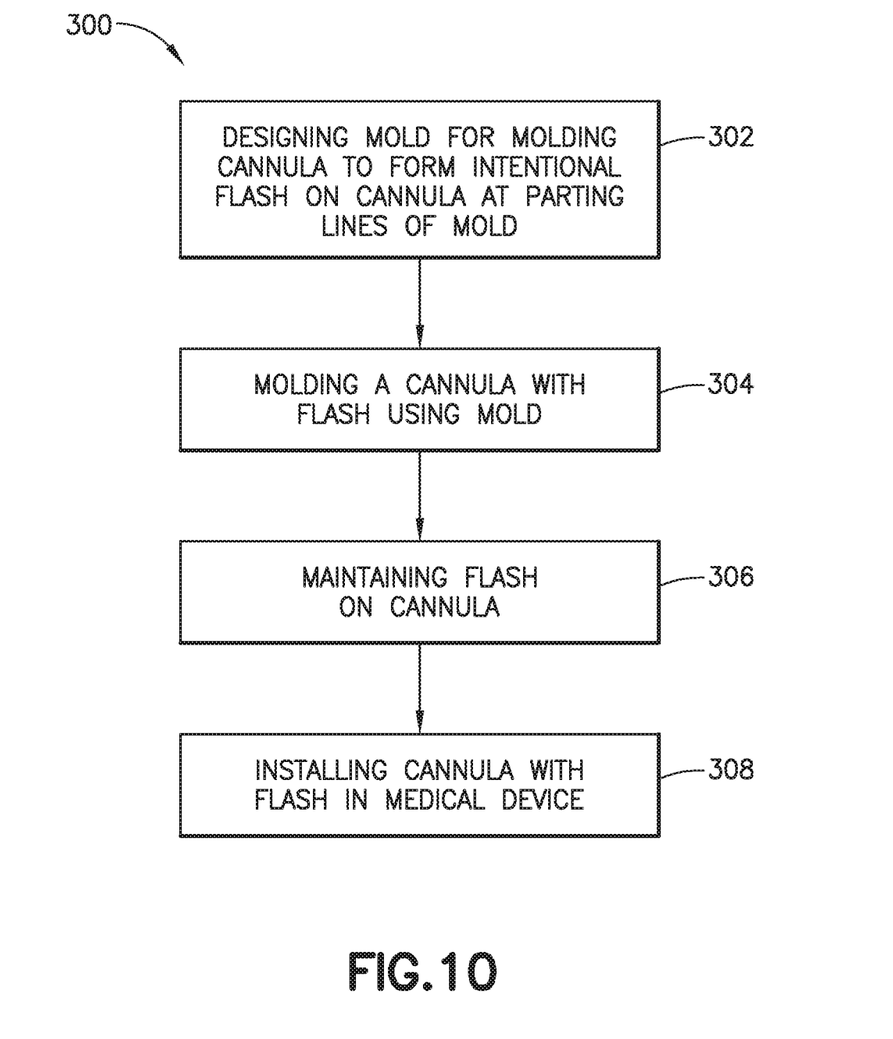

FIG. 10 is a flow chart illustrating a method 300 in accordance with another embodiment of the present invention. Operation 302 is designing a mold for molding a cannula to form intentional flash on the cannula at parting lines of the mold. Operation 304 is molding the cannula with flash using the mold. Operation 306 is maintaining the flash on the cannula, and operation 308 is installing the cannula with flash in a medical device, such as base 180. According to one embodiment, the flash is maintained on the cannula without modifying the flash. According to one embodiment, the cannula is installed in the medical device without modifying the flash. According to one embodiment, designing the mold includes designing the mold so that the intentional flash is bladelike. According to one embodiment, the flash is serrated, and according to another embodiment, the intentional flash is smooth.

Although only a few embodiments of the present invention have been shown and described, the present invention is not limited to the described embodiments. Instead, it will be appreciated by those skilled in the art that changes may be made to these embodiments without departing from the principles and spirit of the invention. Any of the embodiments and/or elements disclosed herein may be combined with one another to form various additional embodiments not specifically disclosed, as long as they do not contradict each other. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

The invention claimed is:

1. A method, comprising:
    molding a hollow cannula to create flash on the cannula at parting lines of a mold, the flash having a cutting edge;
    retaining the flash on the cannula; and
    installing the cannula with the flash in a medical device with the flash disposed on an exterior of the medical device.

2. The method according to claim 1, further comprising:
    packaging the medical device having the cannula with the flash.

3. The method according to claim 1, further comprising:
    inserting the cannula with the flash into a patient so that the flash contacts the patient's skin.

4. The method according to claim 1, wherein the flash is serrated.

5. The method according to claim 1, wherein the flash is smooth.

6. The method according to claim 1, wherein a radially outer edge of the flash is serrated.

7. The method according to claim 1, wherein a radially outer edge of the flash is smooth.

8. A method, comprising:
    molding a hollow cannula to create bladelike flash on the cannula at parting lines of a mold;
    retaining the flash on the cannula;
    installing the cannula with the flash in a medical device; and
    modifying a portion of the mold to permit intentional leakage of molding material at the modified portion.

9. A method, comprising:
    designing a mold for molding a cannula for a medical device so that an intentional flash with a cutting edge is formed at parting lines of the mold during molding of the cannula;
    molding the cannula using the mold;
    maintaining the flash on the molded cannula after the molding; and
    installing the molded cannula with the flash in the medical device with the flash disposed on ar exterior of the medical device.

10. The method according to 9, wherein a radially outer edge of the flash is one of serrated and smooth.

11. A method, comprising:
    designing a mold for molding a cannula for a medical device so that an intentional flash is formed at parting lines of the mold during molding of the cannula;
    molding the cannula using the mold;
    maintaining the flash on the molded cannula after the molding; and
    installing the molded cannula with the flash in the medical device:
    wherein designing the mold comprises designing the mold so that the intentional flash is bladelike.

12. The method according to claim 11, wherein the intentional flash is serrated.

13. A hollow cannula made by the process of claim 1.

14. A medical device made by the process of claim 9.

* * * * *

UNITED STATES PATENT AND TRADEMARK OFFICE
CERTIFICATE OF CORRECTION

| | | |
|---|---|---|
| PATENT NO. | : 12,296,109 B2 | Page 1 of 1 |
| APPLICATION NO. | : 17/299860 | |
| DATED | : May 13, 2025 | |
| INVENTOR(S) | : Jeff Reed et al. | |

It is certified that error appears in the above-identified patent and that said Letters Patent is hereby corrected as shown below:

In the Claims

Column 6, Line 44, delete "ar" and insert therefor --an--.

Signed and Sealed this
Fifteenth Day of July, 2025

Coke Morgan Stewart
*Acting Director of the United States Patent and Trademark Office*